United States Patent [19]

Croix

[11] 3,949,005

[45] Apr. 6, 1976

[54] HEXAFLUORO-t-BUTYL-DIFLUOROMETHYL ETHER AS AN INHALATION ANESTHETIC

[75] Inventor: Louise S. Croix, Summit, N.J.

[73] Assignee: Airco, Inc., Montvale, N.J.

[22] Filed: Feb. 27, 1975

[21] Appl. No.: 553,856

Related U.S. Application Data

[60] Division of Ser. No. 468,478, May 9, 1974, Pat. No. 3,883,664, which is a continuation-in-part of Ser. No. 326,481, Jan. 29, 1973, abandoned, which is a continuation of Ser. No. 174,957, Aug. 8, 1971, abandoned.

[52] U.S. Cl. .............................. 260/614 F
[51] Int. Cl.² ................... C07C 43/00; C07C 43/12
[58] Field of Search .................... 260/614 F

[56] References Cited
UNITED STATES PATENTS 3,346,448  10/1967  Gilbert et al. ............... 260/614 F X
3,663,714  5/1972  Terrell ......................... 260/614 F X
3,869,519  3/1975  Terrell ............................ 260/614 F

FOREIGN PATENTS OR APPLICATIONS 735,828  9/1969  Belgium ........................ 260/614 F

*Primary Examiner*—Howard T. Mars
*Attorney, Agent, or Firm*—Roger M. Rathbun; Edmund W. Bopp; H. Hume Mathews

[57] ABSTRACT

Hexafluoro-t-butyl difluoromethyl ether of the formula

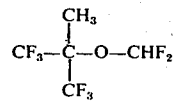

is useful as an inhalation anesthetic.

1 Claim, No Drawings

HEXAFLUORO-T-BUTYL-DIFLUOROMETHYL ETHER AS AN INHALATION ANESTHETIC

This application is a division of Application Serial No. 468,478, filed May 9, 1974 now patent No. 3883664 which is a continuation-in-part of application Serial No. 326,481, filed Jan. 29, 1973, and now abandoned, which is a continuation of application Ser. No. 174,957, filed Aug. 8, 1971 and now abandoned.

This invention relates to hexafluoro-t-butyl difluoromethyl ether and its use in producing anesthesia in anesthetic-susceptible mammals. The chemical formula for this ether is

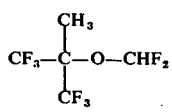

The compound of the present invention lends itself to effective use as an inhalant anesthetic in respirable mixtures containing life-supporting concentrations of oxygen, with or without other inhalation anesthetics, such as nitrous oxide. Administration of the compound may be by any of the well known techniques for administering general inhalation anesthetics, for example, by using the open drop, semi-closed, or closed systems.

The effective amount of the compound of this invention to be employed depends on the level of anesthesia to which the mammal is to be brought, the rate at which anesthesia is to be induced, and the length of time over which anesthesia is to be maintained. Minor volume percentages, generally about 4 or somewhat more volume percent of the compound in oxygen, can often be employed. The amount used should be sufficient to provide a significant anesthetic effect but not so much as to produce unacceptable deleterious side effects. The amount of anesthetic to be used can be regulated, starting with a small amount of the ether and gradually increasing the amount until the desired plane of anesthesia is reached. By then monitoring the physical reactions of the mammal, as is the usual procedure, the duration and plane of anesthesia can be readily controlled.

The ether compound of this invention is also easily miscible with other organic liquids, including fats and oils, and has useful solvent properties, for example, as a solvent for fluorinated olefins and other fluorinated materials, such as fluoro waxes. The compound of this invention may be used to prepare pastes and dispersions of such materials useful for coatings and the like, and may be used as a degreasing agent. In the latter capacity, for example, the ether compound of this invention can be used as a solvent to remove grease or other oily substances from a metal surface that is to be painted.

The hexafluoro-t-butyl difluoromethyl ether of this invention can be made by reacting hexafluoro-t-butanol with fluorodichloromethane. As an example of a specific synthesis of the compound of this invention, into the liner of a 1 liter stainless steel autoclave was placed 182 g. (1 mole) of commercially obtained hexafluoro-t-butanol and 50 g. of methyl pyrrolidone as a solvent. The sealed autoclave was stirred while 86.5 g. (1 mole) of commercially obtained fluorodichloromethane was added as a liquid (74 ml.) through a pressure burette. A 50% solution of NaOH (243 g., 3 moles) followed at such a rate as to maintain the reaction temperature at 30°–40°C. with outside cooling. After an additional 1 hour of stirring at 35°C., the autoclave was opened and the contents distilled. From the first fraction (51 g., bp: 62°–3°C.) was separated by preparative chromatography 26.7 g. of $(CF_3)_2(CH_3)C-O-CHF_2$.

Calculated for $C_5H_4F_8O$: C, 25.9; H, 1.7; F, 65.5; Found: C, 26.1; H, 1.8; F, 65.4

This normally liquid compound has a boiling point of 70°C., a specific gravity of 1.50, a vapor pressure at 25°C. of 140 mm. Hg, and a refractive index ($n_D^{20}$) of 1.2847. The compound is odorless and borderline as regards flammability.

In order to determine the potency of the aliphatic ether of the present invention as an inhalation anesthetic in combination with oxygen, tests were carried out on mice. The sample tested was at least 99.5% pure as determined by vapor phase chromatography. In the tests, the ether compound is administered to test mice by a standard procedure in which a measured quantity of the agent is placed in a laboratory jar and allowed to completely vaporize so as to give a calculated vapor concentration. The test mice are then quickly placed in the jar and observed. Anesthesia is determined by observing the righting reflex of the mice. Recovery time is measured beginning when the mice are transferred from the test jar to room air and ending when the mice are observed to be able to walk.

In such tests, the hexafluoro-t-butyl difluoromethyl ether, when used at a vapor concentration of 2.5%, induced a very light anesthesia in 1 minute, 37 seconds. There was moving throughout maintenance of the anesthesia, and recovery therefrom required 15 seconds. At 4.0%, the induction time was 59 seconds and the recovery time was 39 seconds. Again, there was moving throughout maintenance. When used at a vapor concentration of 8.0%, the induction time was shortened to 19 seconds and the recovery period lengthened to 2 minutes, 13 seconds. Maintenance was accompanied by respiratory depression and, once again, by moving of the subjects, thus indicating that the use of larger concentrations might be desirable in some circumstances.

Since volatile general anesthetics today are generally administered in a closed system involving recycling the exhaled gases for conservation of the relatively expensive agents and protection of operating room personnel, it is required that commercially useful volatile anesthetics intrinsically have good soda-lime stability as does the compound of the present invention. The compound of the present invention, $(CF_3)_2C(CH_3)OCHF_2$, was subjected to soda-lime for a period of 18 hours to determine its soda-lime stability. The soda-lime was analyzed before and after the test for fluoride ion content. One hundred eighty-eight parts per million fluoride was found to be present before the test and 214 parts per million after the test. These results establish that the tested compound exhibited negligible fluoride ion loss and excellent soda-lime stability.

While there has been described what are at present considered to be preferred embodiments of the invention, it will be understood that various modifications may be made therein which are within the true spirit and scope of the invention.

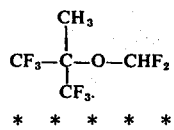

I claim:

1. Hexafluoro-t-butyl difluoromethyl ether of the formula: